(12) United States Patent
Lin et al.

(10) Patent No.: US 9,186,817 B2
(45) Date of Patent: Nov. 17, 2015

(54) METHOD FOR PREPARING TOBRAMYCIN SULFATE POWDER

(71) Applicant: SCI Pharmtech, Inc., Taoyuan (TW)

(72) Inventors: Yen-Chih Lin, Taoyuan (TW); Yon-Lian Wu, Taoyuan (TW)

(73) Assignee: Sunny Pharmtech Inc., New Taipei (TW)

( * ) Notice: Subject to any disclaimer, the term of this patent is extended or adjusted under 35 U.S.C. 154(b) by 198 days.

(21) Appl. No.: 13/957,107

(22) Filed: Aug. 1, 2013

(65) Prior Publication Data

US 2015/0035182 A1 Feb. 5, 2015

(51) Int. Cl.
*A61K 9/14* (2006.01)
*A61K 31/7036* (2006.01)
*B29B 7/76* (2006.01)
*A61K 9/00* (2006.01)
*A61K 9/16* (2006.01)

(52) U.S. Cl.
CPC ............... *B29B 7/76* (2013.01); *A61K 9/0019* (2013.01); *A61K 9/14* (2013.01); *A61K 31/7036* (2013.01); *A61K 9/1682* (2013.01)

(58) Field of Classification Search
None
See application file for complete search history.

(56) References Cited

U.S. PATENT DOCUMENTS

| | | |
|---|---|---|
| 2003/0129140 A1* | 7/2003 | Tarara et al. ............ 424/46 |
| 2005/0069591 A1* | 3/2005 | Bernstein et al. .......... 424/489 |
| 2010/0075913 A1* | 3/2010 | Deboeck et al. .......... 514/29 |
| 2011/0200678 A1* | 8/2011 | Hwang et al. ............ 424/489 |
| 2013/0243828 A1* | 9/2013 | Lipp et al. ............... 424/400 |
| 2014/0005135 A1* | 1/2014 | Prestrelski et al. ........ 514/40 |
| 2014/0134253 A1* | 5/2014 | Lai et al. ................. 424/489 |

\* cited by examiner

*Primary Examiner* — Mary F Theisen
(74) *Attorney, Agent, or Firm* — Leydig Voit & Mayer, Ltd.

(57) ABSTRACT

A method for preparing tobramycin sulfate powder for injection is provided. The method includes steps of providing a sterile tobramycin sulfate solution; and aseptically spray drying the tobramycin sulfate solution to obtain the tobramycin sulfate powder.

10 Claims, 4 Drawing Sheets

METHOD FOR PREPARING TOBRAMYCIN SULFATE POWDER

FIELD OF THE INVENTION

This invention relates to methods for preparing powder for injection. In particular, the present invention relates to a method for preparing tobramycin sulfate powder by spray drying.

BACKGROUND OF THE INVENTION

Tobramycin is a very hygroscopic aminoglycoside antibiotic that is extracted from the fermentation of *Streptomyces tenebrarius*. Two major impurities and a degradation product specified in European Pharmacopeia (EP) are kanamycin B, neamine (impurities), and nebramine (degradation product), respectively. It shows an antibacterial effect on the gram-negative bacteria when formulated as ophthalmic, inhalant, and injectable dosage forms. Generally, the injectable dosage forms of tobramycin include Tobramycin Injection and Tobramycin for Injection. The former one is a tobramycin sulfate solution with the addition of preservatives and antioxidants, and the latter one is tobramycin sulfate powder without any other excipients. As the Tobramycin for Injection is concerned, it is generally prepared by lyophilizing (freeze-drying) a sterile tobramycin sulfate solution. Although the lyophilization process for powder for injection is well-developed in pharmaceutical industry, it is still inefficient on drying and requires high energy consumption. Moreover, low throughput is another demerit due to the long cycle time, i.e., about 24 to 48 h. Thus, the lyophilization process is essentially time-consuming and expensive.

Spray drying is one of the conventional techniques in chemical industry since 1920s and has several advantages, compared to the lyophilization process. For example, the spray drying process can save more than 50% energy cost in comparison to the lyophilization process. Generally, the spray drying process mainly includes three stages. The first one is the atomization of the concentrated solution into numerous liquid droplets. Second, the liquid droplets contact with the heated gas, e.g., air or $N_2$, and then the liquid droplets evaporate to accompany with the nucleation of particles in a short period about a few seconds. Finally, the dried particles are collected by a cyclone system incorporated with a bag filter or wet scrubber. In view of industrial processes, the advantages of spray drying include the continuous mass production, automated controlling, higher energy efficiency, and feasible applications for both heat-resistant and heat-sensitive materials. Therefore, the application of spray dryers is widely adopted in industry. However, it is rarely in the aspect of manufacturing active pharmaceutical ingredients (APIs) so far.

In 2008, Pilcer had reported that tobramycin suspension can be spray dried to prepare tobramycin powder for inhalation in his dissertation. In the study, tobramycin suspensions were firstly prepared by using a homogenizer to disperse tobramycin powder into isopropanol solutions containing 0 to 20% (v/v) water. After the tobramycin suspension was spray dried, the prepared powders were filled with capsules as the tobramycin powder for inhalation. The same results were also disclosed in other publications.

The above prior art described the preparation of tobramycin powder for inhalation by spray drying a tobramycin suspension, in which isopropanol is used as continuous phase. However, the prepared tobramycin powder is different from tobramycin sulfate and not suitable for intravenous use in consideration of the residual isopropanol, which is toxic to health. Also the chosen isopropanol is a flammable solvent which increases the possibility of explosion during spray drying. In addition, isopropanol is not environmentally friendly. On the other hand, the solid content of prepared tobramycin suspension is merely 5% (w/v) which is much lower than the saturated solubility of tobramycin in water. Thus the production rate of spray drying tobramycin is quite low and impractical. Moreover, the injectable dosage form, i.e., powder for injection, is used more widely in comparison to the dry powder inhalation (DPI) due to its effectiveness and ready-to-use.

Accordingly, the present invention provides a method of spray drying for preparing tobramycin sulfate powder that can be formulated as Tobramycin for Injection and reconstituted for intravenous administration.

SUMMARY OF THE INVENTION

The present invention provides a method for preparing tobramycin sulfate powder. The method includes steps of: providing a sterile tobramycin sulfate solution; aseptically spray drying the tobramycin sulfate solution to obtain tobramycin sulfate powder that can be collected by a cyclone system incorporated with a wet scrubber. The prepared tobramycin sulfate powder can be formulated as Tobramycin for Injection and reconstituted for intravenous and intramuscular administration.

Preferably, the present invention further comprises steps of: dissolving the tobramycin powder in water to obtain a tobramycin solution; mixing the tobramycin solution and a sulfuric acid solution to form a tobramycin sulfate solution; and aseptically filtrating the tobramycin sulfate solution by a membrane filter.

Preferably, the tobramycin powder is made of tobramycin hydrate or tobramycin anhydrate.

Preferably, the sulfuric acid solution and the tobramycin solution are mixed with a molar ratio of sulfuric acid to tobramycin in a range between 1.10 and 2.50.

Preferably, the tobramycin sulfate solution has a concentration in a range from 4 wt % to 40 wt %.

Preferably, the tobramycin sulfate solution has a temperature in a range from 5° C. to 40° C.

Preferably, the step of aseptically spray drying the tobramycin sulfate solution is performed at an inlet temperature of drying gas in a range from 80° C. to 240° C. In various embodiments of the present application, the step of aseptically spray drying the tobramycin sulfate solution is performed with a drying gas selected from air, nitrogen, and inert gas.

Preferably, the tobramycin sulfate powder has an amorphous structure or a partially amorphous structure.

In accordance with the embodiments of the present invention, the method is constructed to manufacture tobramycin sulfate powder that can be formulated as Tobramycin for Injection and reconstituted for intravenous administration.

DETAILED DESCRIPTION OF THE PREFERRED EMBODIMENT

The present invention provides a method for preparing the tobramycin sulfate powder by spray drying and such powder can be used as tobramycin for injection or reconstituted as tobramycin injection for IV administration. In the following preferred embodiments, the invention is specifically described. However it is not limited to the embodiments.

In the preferred embodiments of the invention, the tobramycin free base powder with an assay of 940 μg/mg and water content of 4.5% is supplied from a pharmaceutical company listed on the Drug Master Files (DMFs) of tobramycin API. It meets the quality specification of tobramycin in United State Pharmacopeia (USP). The sulfuric acid solution and Water for Injection are available from local suppliers.

EXAMPLE 1

In the preferred embodiments, the spray dryer, SD-06AG (from LabPlant UK Ltd.), mainly contains a peristaltic pump, a nozzle, a compressor, a blower, an electric-wire heater, a drying chamber and cyclone. In addition, a wet scrubber built by a local company is connected to the gas outlet of the spray dryer in order to recover the uncollected spray dried powder from cyclone. At the beginning of the spray drying process, the spray dryer was actuated in the preferred conditions and maintained for 30 min in order to achieve heat balance therein. In the meanwhile, the tobramycin powder was dissolved in water in a flask filled with nitrogen, and then the tobramycin solution was mixed with sulfuric acid to form a tobramycin sulfate solution. The tobramycin sulfate solution was further stirred for 15 min at a temperature ranged from 5° C. to 40° C., and then filtrated by a membrane filter with a pore size less than or equal to 0.2 μm. After that, the spray dryer was charged with the tobramycin sulfate solution. The fed tobramycin sulfate solution was atomized by a two-fluid nozzle to form numerous liquid droplets in a drying chamber, and then tobramycin sulfate powder precipitated with the evaporation of water and nucleation of tobramycin sulfate for a short period about milliseconds to a few seconds. The prepared tobramycin sulfate powder was collected by a cyclone system incorporated with a wet scrubber. Finally, The prepared tobramycin sulfate powder was maintained in a collector for 15 min for another heat balance after the tobramycin sulfate solution was drained out, and then the tobramycin sulfate powder was unload in a collector. The tobramycin sulfate powder was examined by the reported analytical HPLC method in the current USP monograph for tobramycin, and measured by Karl Fischer titrator. In addition, the absorbance is also utilized as a quantification tool for the discoloration of reconstituted solution.

EXAMPLE 2

Figure 1:
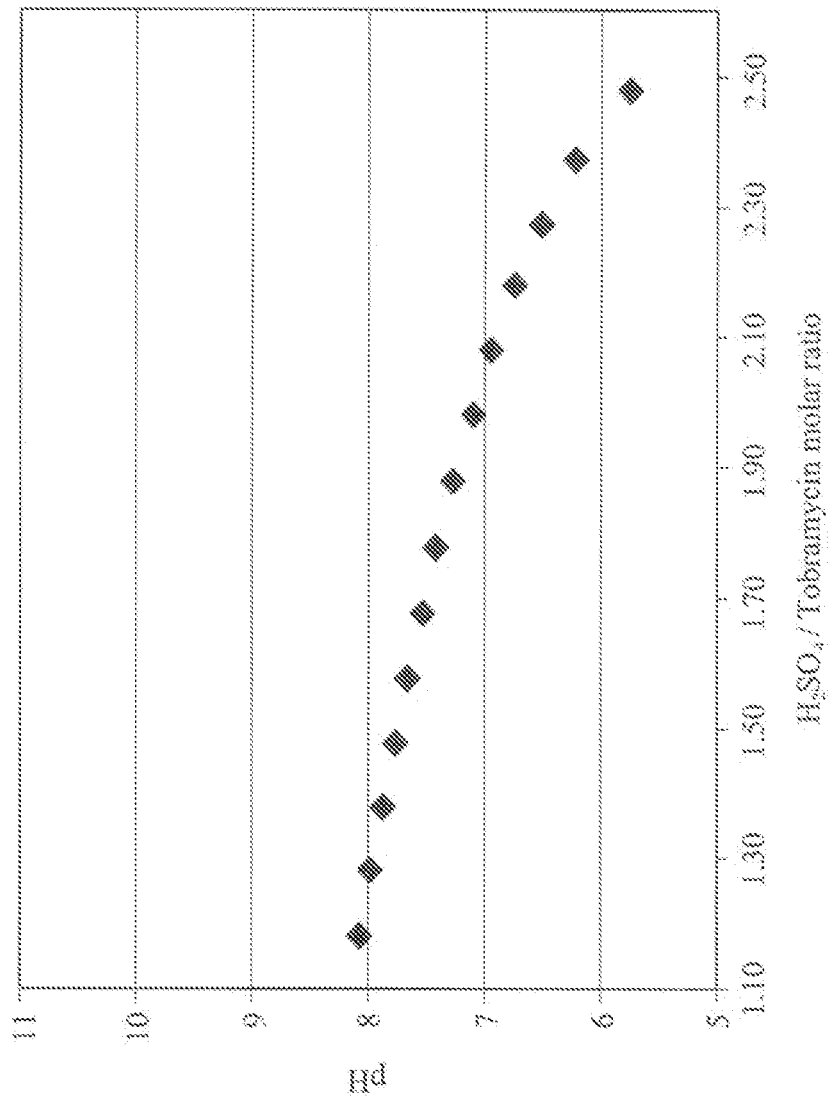
FIG. 1 shows the effects of $H_2SO_4$/tobramycin molar ratios on the pH value of constituted tobramycin sulfate solution according to the present invention.

The pH value of each constituted solution containing 40 mg tobramycin/ml was controlled by the ratio of $H_2SO_4$/tobramycin as shown in FIG. 1. Thus the composition of tobramycin sulfate powder was modified by adjusting the molar ratio of $H_2SO_4$/tobramycin. Due to the specified pH ranged from 6.0 to 8.0, the molar ratio of $H_2SO_4$/tobramycin was controlled in a range from about 1.10 to about 2.50.

In addition to the specified ratio of $H_2SO_4$/tobramycin, the concentration of tobramycin sulfate solution was about 4 wt % to about 40 wt %, more particularly about 6 wt % to about 30 wt %. In the process of preparing the tobramycin sulfate solution, the system was filled with nitrogen gas in order to prevent the contact of air or oxygen with the tobramycin solution, which is isothermal at 25° C.

A 30 wt % tobramycin sulfate solution with a $H_2SO_4$/tobramycin molar ratio of 2.4 was spray dried by using air as the drying gas in the form of co-current, at an inlet temperature of 200° C. for drying gas, a liquid flow rate of 192 ml/h, and a gas flow rate of 42 CMH. The spray dried tobramycin sulfate powder had the water content of 3.24% and the yield was 45%. Also the measured content of impurities remained the same as that in tobramycin API. Furthermore, the tobramycin sulfate powder was reconstituted as a solution containing 40 mg tobramycin/ml and the measured pH was 6.46 within the pH specification of tobramycin for injection in USP.

EXAMPLE 3

Figure 2:
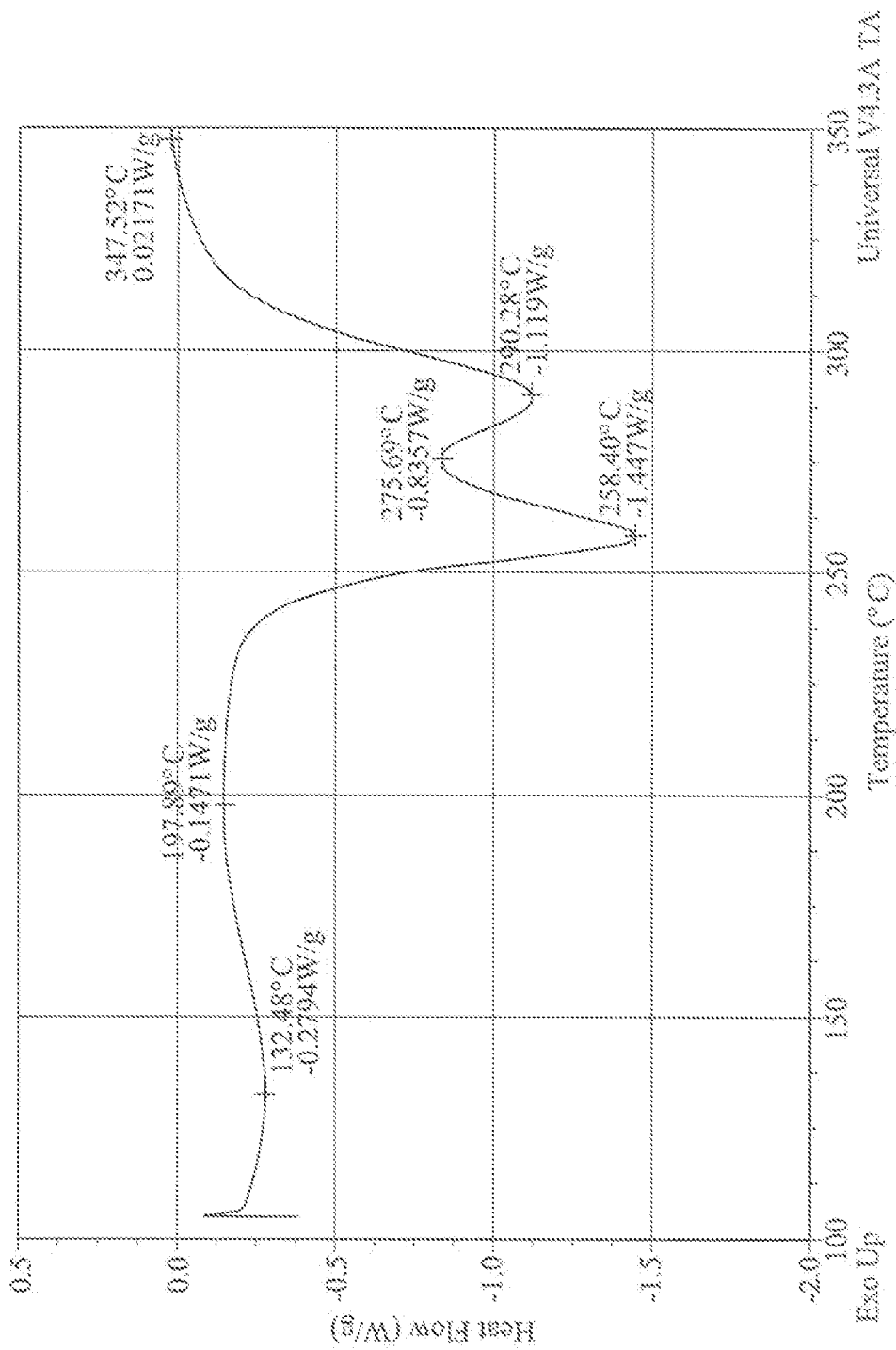
FIG. 2 shows a thermogram obtained from Differential Scanning calorimetry for spray dried tobramycin sulfate powder according to the present invention.
Figure 3:
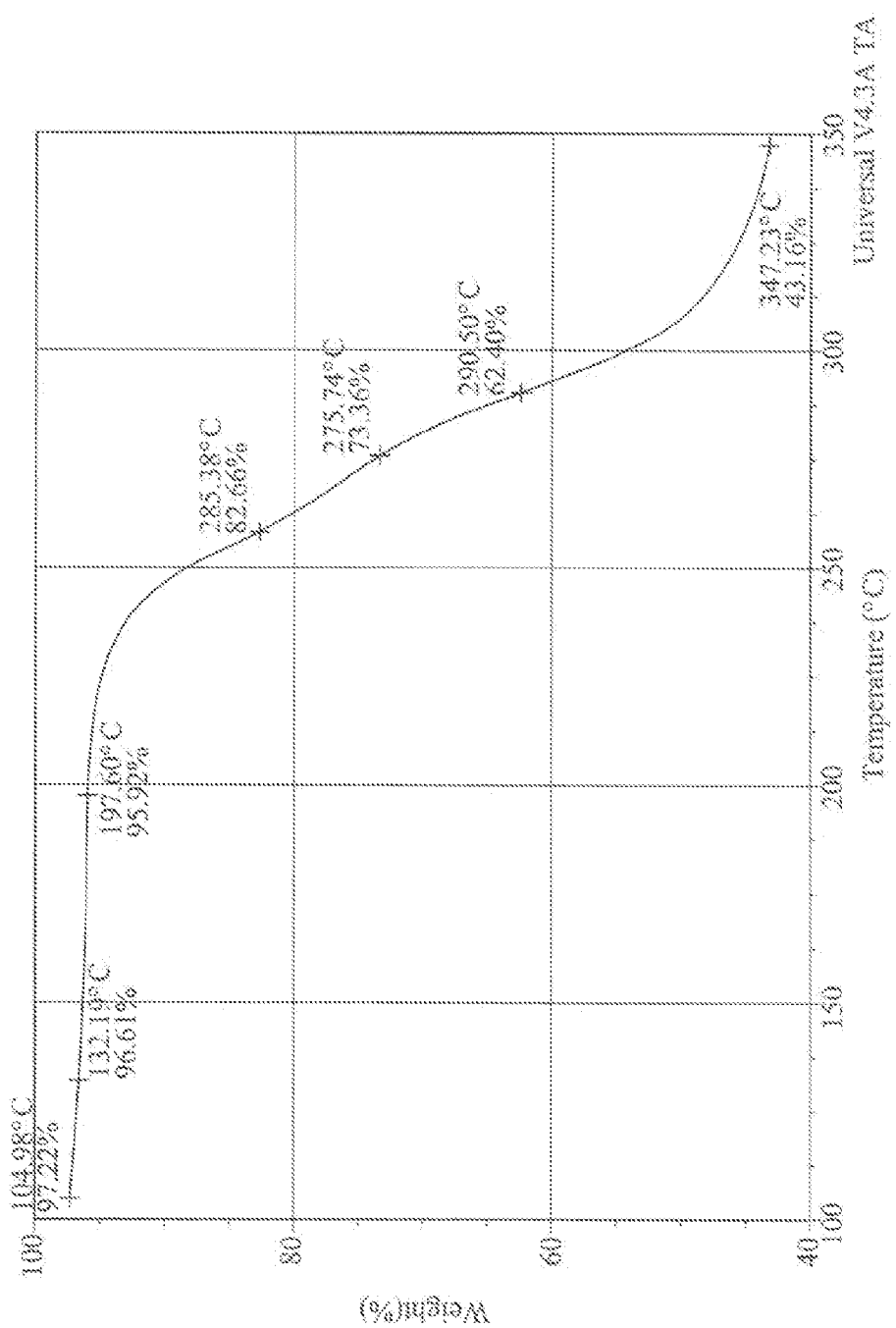
FIG. 3 shows a thermogravimetric analysis for spray dried tobramycin sulfate powder according to the present invention.
Figure 4:
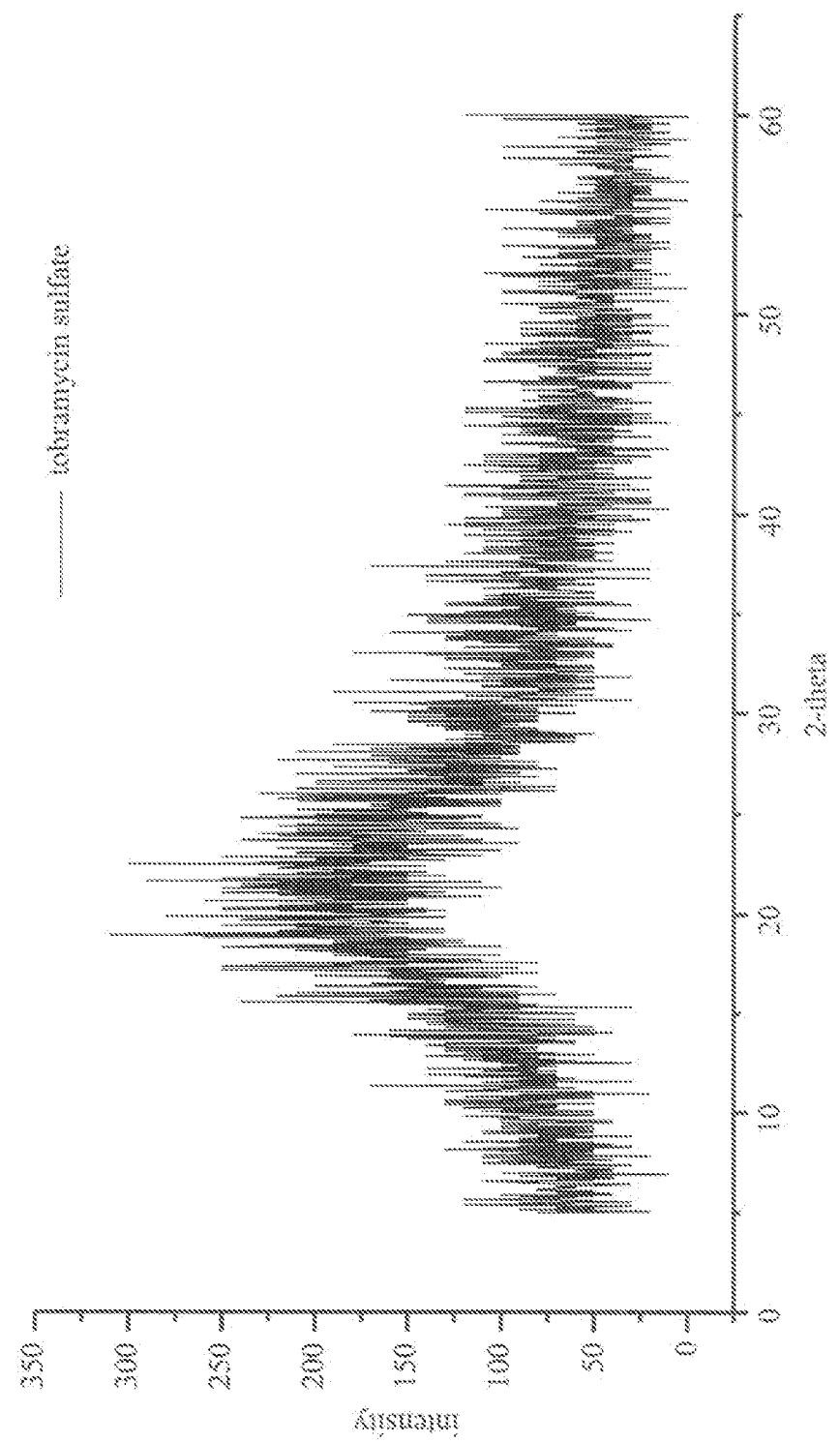
FIG. 4 shows a X-ray diffraction pattern of spray dried tobramycin sulfate powder.

In another embodiment, nitrogen was used as the drying gas in the spray dryer and the other conditions remained the same as those in EXAMPLE 2. The resultant tobramycin sulfate powder had the water content of 1.86% and the yield was 59%. Moreover, the spray dried tobramycin sulfate powder was further dried by a rotary-evaporator in vacuum to obtain powder with about 0.95% water content within the specification in USP. In addition, the thermal property of tobramycin sulfate powder was analyzed by Differential Scanning calorimeter (DSC) and Thermogravimetric Analyzer (TGA). The DSC thermograph of FIG. 2 represented that the tobramycin sulfate powder had an endothermic melting point between 258° C. and 290° C. overlapping with an exothermic oxidation one at about 276° C. Furthermore, the TGA result in FIG. 3 revealed that the weight loss for oxidation of tobramycin sulfate powder had initiated at temperature higher than 200° C. In addition to the above thermal properties, the crystal structure of tobramycin sulfate powder was characterized by X-ray diffraction pattern in FIG. 4. Apparently, the amorphous form of the spray dried tobramycin sulfate powder is attributed to the fast evaporation rate of water and rapidly primary nucleation of cluster during the short drying period. Finally, the tobramycin sulfate powder was reconstituted as a solution containing 40 mg tobramycin/ml and the pH of the solution was 6.49.

EXAMPLE 4

In another embodiment of the present application, a 6 wt % tobramycin sulfate solution and 392 ml/h liquid flow rate were used, and the other parameters remained the same as those in EXAMPLE 3. After spray drying, the tobramycin sulfate powder still had the water content of 4.38% and the yield was about 62%. Also the resultant powder was reconstituted to a tobramycin sulfate solution containing 40 mg tobramycin/ml. As to the pH and related impurities in the reconstituted solution, they were within the USP specifications.

EXAMPLE 5

In another embodiment of the present application, the inlet temperature of drying gas was controlled at 100° C. The other conditions including the drying gas, the $H_2SO_4$/tobramycin molar ratio, the liquid flow rate, and the gas flow rate were the same as those in EXAMPLE 3. The spray dried powder contained 5.58% residual water and the yield was about 47%. Furthermore, the spray dried tobramycin sulfate powder was continuously dried by a rotary-evaporator in vacuum. Thus the water content of the dried powder was decreased to about 1.34%. In addition, the bulk density and tapped density were measured to estimate the flowability of tobramycin sulfate powder according to the Carr's index. The analysis showed that the bulk density and tapped density were 0.43 g/cm$^3$ and 0.53 g/cm$^3$, respectively. Accordingly the Carr's index of tobramycin sulfate powder was about 18.8 that represents a fair flowability. Moreover, with respect to the impurities and pH of the reconstituted tobramycin sulfate solution containing 40 mg tobramycin/ml as shown in Table 1, the spray dried tobramycin sulfate powder had an acceptable quality within the specifications provided by USP. In addition, the difference of absorbance in Table 1 was insignificant so that the discoloration of reconstituted solution was not a concern.

TABLE 1

| EXAMPLE 5 | Tobramycin sulfate solution constituted from tobramycin free base | Tobramycin sulfate solution reconstituted from spray dried tobramycin sulfate |
|---|---|---|
| Nebramine (HPLC, %) | 0.07% | 0.06% |
| pH of solution | 6.22 | 6.56 |
| Absorbance at 400 nm incident light | 0.027 | 0.038 |

What is claimed is:

1. A method for preparing tobramycin sulfate powder for injection, comprising steps of:
   dissolving tobramycin powder in water to obtain a tobramycin solution;
   mixing the tobramycin solution and a sulfuric acid solution to form a tobramycin sulfate solution;
   aseptically filtrating the tobramycin sulfate solution to form a sterile tobramycin sulfate solution; and
   aseptically spray drying the sterile tobramycin sulfate solution to obtain the tobramycin sulfate powder.

2. The method according to claim 1, wherein the sterile tobramycin sulfate solution is obtained by
   using a membrane filter to aseptically filtrate the tobramycin sulfate solution.

3. The method according to claim 1, wherein the tobramycin powder is made of tobramycin hydrate or tobramycin anhydrate.

4. The method according to claim 1, wherein the sulfuric acid solution and the tobramycin solution are mixed with a molar ratio of sulfuric acid to tobramycin in a range of from 1.10 to 2.50.

5. The method according to claim 1, wherein the tobramycin sulfate solution has a concentration in a range of from 4 wt % to 40 wt %.

6. The method according to claim 5, wherein the tobramycin sulfate solution has the concentration in a range of from 6 wt % to 30 wt %.

7. The method according to claim 1, wherein the tobramycin sulfate solution has a temperature in a range of from 5° C. to 40° C.

8. The method according to claim 1, wherein the step of aseptically spray drying the tobramycin sulfate solution is performed at an inlet temperature of drying gas in a range of from 80° C. to 240° C.

9. The method according to claim 1, wherein the step of aseptically spray drying the tobramycin sulfate solution is performed with a drying gas selected from the group consisting of air, nitrogen, and inert gas.

10. The method according to claim 1, wherein the tobramycin sulfate powder has an amorphous structure or a partially amorphous structure.

* * * * *